(12) United States Patent
List

(10) Patent No.: US 8,231,645 B2
(45) Date of Patent: Jul. 31, 2012

(54) LANCET DEVICE

(75) Inventor: Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 957 days.

(21) Appl. No.: 12/048,356

(22) Filed: Mar. 14, 2008

(65) Prior Publication Data

US 2008/0228212 A1 Sep. 18, 2008

(30) Foreign Application Priority Data

Mar. 14, 2007 (EP) .................................... 07005231

(51) Int. Cl.
*A61B 17/34* (2006.01)
*A61B 5/151* (2006.01)
(52) U.S. Cl. ...................................................... 606/182
(58) Field of Classification Search .................. 600/583; 606/167, 170–171, 181–182, 184–186
See application file for complete search history.

(56) References Cited

U.S. PATENT DOCUMENTS

| 5,147,375 | A | 9/1992 | Sullivan et al. |
| 6,080,172 | A | 6/2000 | Fujiwara et al. |
| 6,364,889 | B1 | 4/2002 | Kheiri et al. |
| 2003/0199911 | A1* | 10/2003 | Boecker et al. ............... 606/181 |
| 2004/0098009 | A1* | 5/2004 | Boecker et al. ............... 606/181 |

FOREIGN PATENT DOCUMENTS

| JP | 328168/1998 | 12/1998 |
| WO | WO 02/100460 | 12/2002 |
| WO | WO 2007/006399 | 1/2007 |

OTHER PUBLICATIONS

Office Action, JP Patent Application No. 328168/1998; Aug. 31, 2010. (Partial Translation).

* cited by examiner

*Primary Examiner* — Ryan Severson
*Assistant Examiner* — Ashley Cronin
(74) *Attorney, Agent, or Firm* — Bose McKinney & Evans LLP

(57) ABSTRACT

The present invention relates to lancet device by which a lancet is displaceable along a piercing path to generate a piercing wound in a skin surface, in particular to obtain body fluid for diagnostic purposes. To achieve performance of a piercing movement which is low in noise and shock, the lancet drive may include a control unit for regulating the piercing depth of the lancet and the lancet may be implemented to oscillate freely out in the piercing direction without delimitation by a mechanical piercing depth stop.

25 Claims, 2 Drawing Sheets

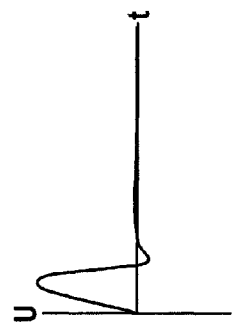
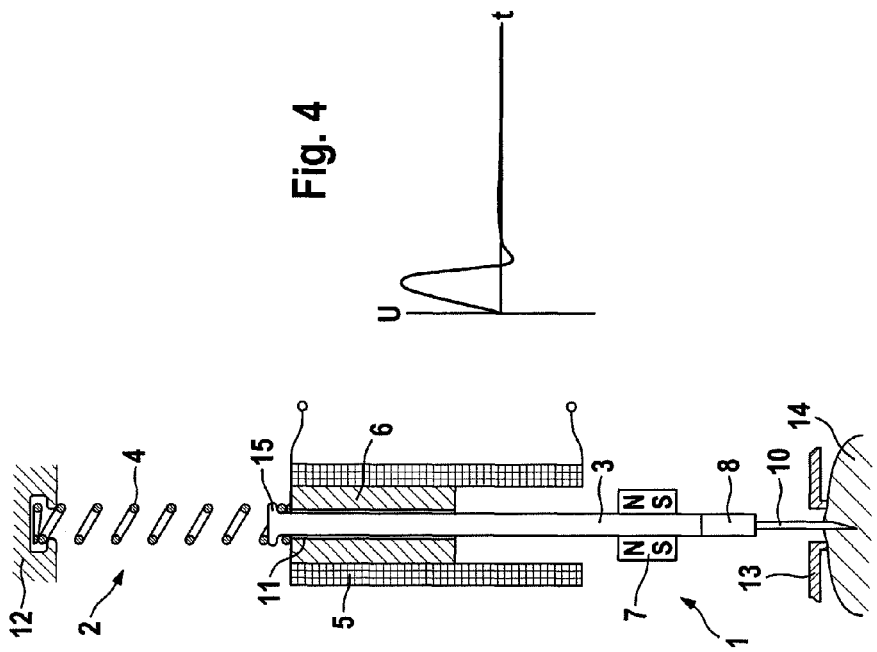
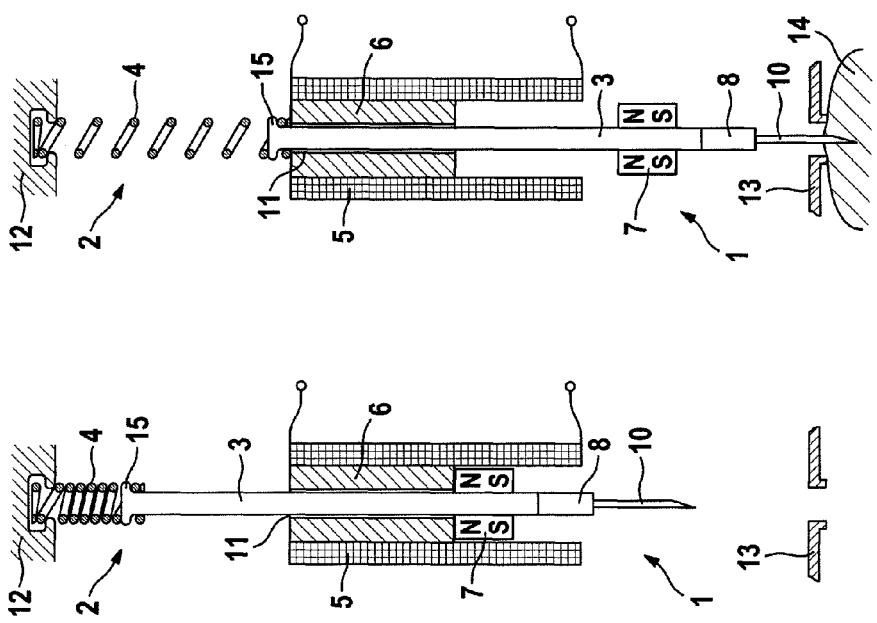
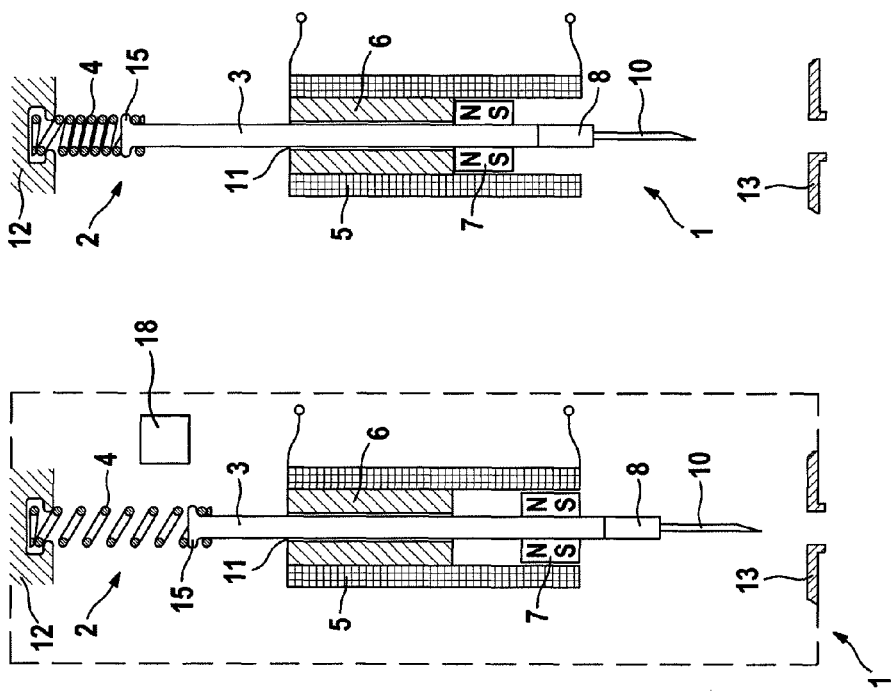

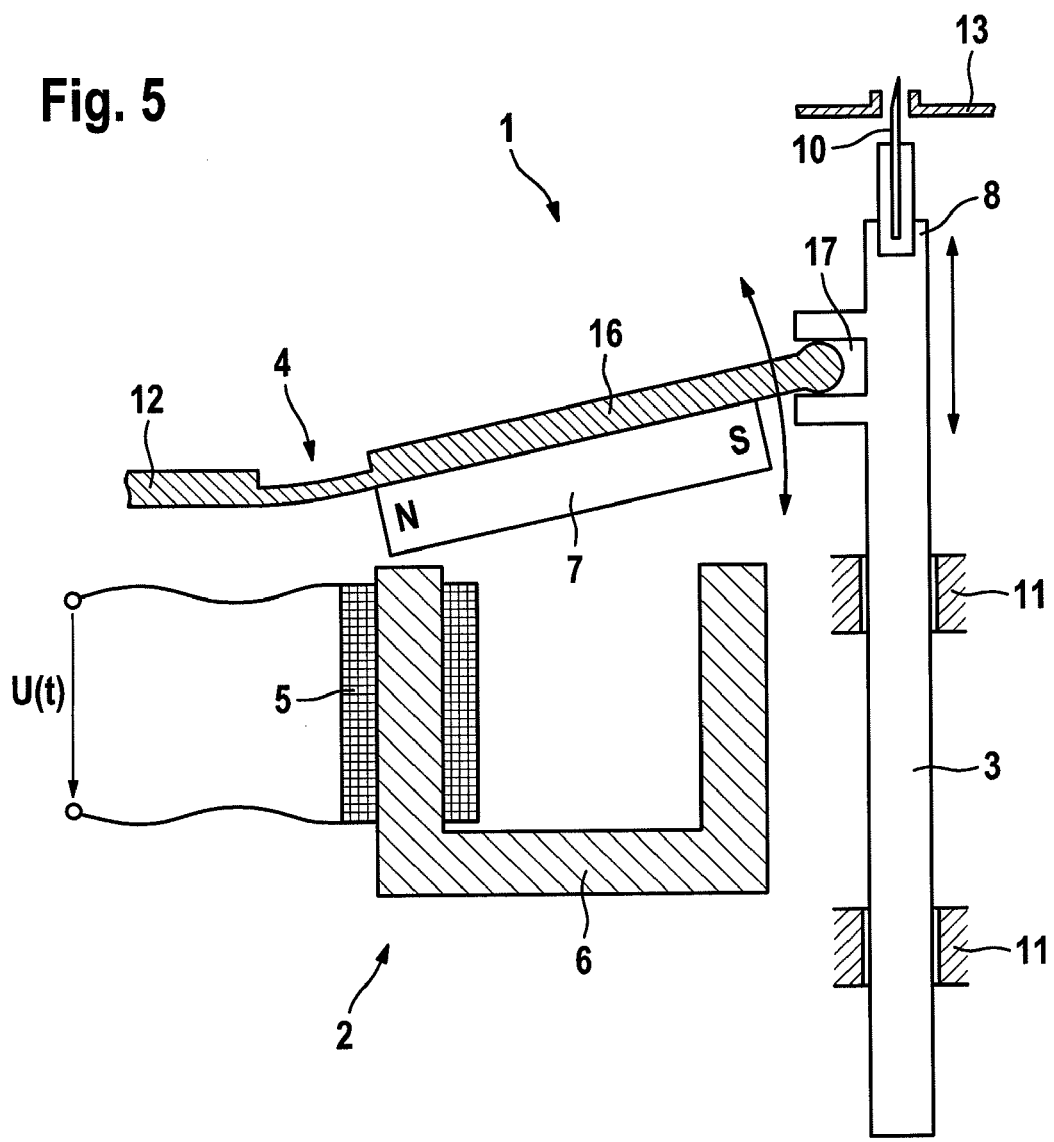

LANCET DEVICE

RELATED APPLICATIONS

This application claims priority to EP 07 005 231.1, filed Mar. 14, 2007, which is hereby incorporated herein by reference.

BACKGROUND

The present invention relates to a lancet device by which a lancet can be displaced along a piercing path to generate a piercing wound in a skin surface, in particular to obtain body fluid for diagnostic purposes, comprising a lancet drive, which has a drive for generating a drive force for a piercing movement of the lancet along the piercing path in the direction toward the skin surface, a retention means for generating a magnetic retention force for retaining the lancet in a tensioned position, and a trigger by which the retention force is reducible enough that the lancet is accelerated in the direction toward the skin surface under the effect of the drive force generated by the drive means.

Furthermore, the present invention relates to a method for operating a lancet device, by which a lancet is displaced along a piercing path to generate a piercing wound in a skin surface, in particular, to obtain body fluid for diagnostic purposes, comprising a lancet drive, by which a drive force is generated for a piercing movement of the lancet along the piercing path in the direction toward the skin surface by the lancet drive, a magnetic retention force is generated for retaining the lancet in a tensioned position by retention means, and the retention force is reduced enough by a triggering means that the lancet is accelerated in the direction toward the skin surface under the effect of the drive force generated by the lancet drive.

Lancet devices are required, for example, by diabetics, who have to check their blood sugar level frequently to be able to keep it within specific setpoint limits by insulin injections. Extensive scientific experimentation has proven that a dramatic reduction of the most severe long-term complications of diabetes mellitus (such as retinopathy with resulting blinding of the patient) may be achieved using an intensive treatment having at least four analyses per day.

For users of lancet devices, it is desirable on one hand to create the least amount of pain possible from piercing, and on the other hand to create the simplest possible operation and ability to handle the lancet device. These issues are of great significance.

A requirement for low-pain piercing is a piercing movement that is as rapid as possible and that has a short dwell time of the lancet in the skin. The use of drive springs has been proven in the prior art to produce a correspondingly strong acceleration of lancets. A disadvantage of lancet devices of this type is that manually tensioning the drive springs after completed piercing is cumbersome for many users. This is true in particular for people whose manual dexterity is restricted by age or illness.

A lancet device in which the drive spring is automatically tensioned by an electric motor offers increased user comfort in this regard, but has the disadvantage that it is larger and heavier due to the electric motor. A lancet device having an integrated electric motor therefore represents a burden for the user who must carry it around continuously for frequent measurements. In addition, production costs are significantly increased by an electric motor.

Furthermore, lancet devices are known in the prior art in which the drive force is generated electromagnetically using a coil. Lancet devices of this type are disclosed, for example, in WO 02/100460 A2 and U.S. Pat. No. 6,364,889. To cause a sufficiently rapid piercing movement for low-pain piercing using electromagnetic lancet drives of this type, strong magnetic fields must be generated. This requires relatively strong electric current flow through the drive coils used, which currents may be generated not at all or only with great effort in a small, compact, handheld device. Electromagnetic lancet drives have therefore been unable to thus far displace the use of mechanical drives having drive springs.

A lancet device having an electromagnetic drive which addresses these disadvantages is known from WO 2007/006399 A1, whose features are referred to herein in regard to advantageous features and designs of lancet drives. The publication relates, inter alia, to the fundamental principle of a piercing drive having a permanent magnet. The drive contains a permanent magnet and electromagnetic coils which allow a compensation of the permanent magnetic field and thus permit control of the drive unit for a piercing aid. The lancet is retained by magnetic forces in a first position and the lancet may no longer be retained in the position by compensation of the magnetic field in the event of corresponding powering of a coil, so that the lancet performs a piercing procedure driven by a spring. The lancet device known from this publication, which may also be referred to as a ballistic piercing aid, has a stop for delimiting the piercing depth, like other known embodiments of ballistic piercing aids. However, this embodiment has multiple consequences and disadvantages:

- Noises arise upon triggering a piercing, e.g., loud clicking. These noises are often perceived as disturbing by users, or may startle the users, which may subjectively increase the sensation of pain from piercing.
- Oscillations are excited in the lancet system, which are transmitted to the lancet stuck into the tissue and may thus cause or increase pain.
- Because the stop is not perfectly inelastic, kinetic energy is transmitted from the stop back to the lancet, because of which the ballistic system comprising the lancet tends to reverberate along the axis of the piercing movement. This may even result in multiple lancet exits, which also cause pain.

To suppress these undesirable accompanying effects, various complex auxiliary devices are required according to the prior art, which make the lancet device or the entire system larger and more expensive to manufacture.

If piercing or lancet devices of this type are to be integrated in a blood analysis unit, it is advisable to incorporate the actions of "tensioning" and "triggering" the lancet in the overall ergonomics, which succeeds especially well if they are operated automatically by the device, and/or may be started by the user using operating elements required in any case for an analysis device. In addition, electrical operating elements (switches, buttons, etc.) may then be placed more easily on ergonomically advisable points of the device exterior than mechanical operating elements to be grasped directly. The outlay for such a piercing device thus rises significantly.

Furthermore, path-controlled piercing aids are known (e.g., under the trade name Softclix®), which may be integrated relatively easily in automatic measuring systems and equipped with auxiliary functions. However, these path-controlled piercing aids always set internal masses into movement whose kinetic energy must ultimately be dissipated, which is performed using stops for functional and space purposes. These systems also cause significant noises.

Furthermore, electrical drives for piercing devices are known, e.g., from the above-mentioned WO 2002/100460. These are relatively quiet because they manage without final stops, but they have the disadvantage that all of the kinetic energy for the piercing, including the movement of the device masses which are required for the movement of the lancet, must be provided directly from the electrical power supply. Large inductances are required for generating the required forces which in turn require high voltages for a rapid current change. Thus, in addition to the energy supply (e.g., battery), a power supply (e.g., a capacitor) must also be housed in the device, which is designed for high voltages and provides the required amount of energy for a piercing procedure. Only approximately half of such an accumulator may be practically used, however. This power supply is thus as large as the energy supply itself in regard to the overall volume. This volume requirement makes it absolutely necessary to minimize the moved masses and the resistances and frictions on the piercing path, which requires additional outlay for the unpacking of piercing elements (lancets) from the sterile packaging. This is problematic because spare volume is not typically available in manually handled, mobile measuring systems for diabetics.

SUMMARY OF THE INVENTION

The present invention provides a cost-effective way in which, in a lancet device of the type cited above having a compact design, a sufficiently rapid piercing movement for a low-pain piercing may be generated, disturbing noises and shocks can be significantly reduced, and the user may be relieved as much as possible from preparatory handling, such as tensioning a drive spring.

Exemplary embodiments include a lancet device having a lancet drive comprising a control unit for regulating the piercing depth of the lancet, by which the reduction of the retention force is controllable in such a way that the desired piercing depth of the lancet results as a function of the control unit upon the triggered piercing movement.

According to a further exemplary feature, which may be used in a lancet device of the type cited above and independently of other exemplary embodiments, the lancet may be implemented to freely advance or oscillate in the piercing direction up to an oscillation reversal point, so that the piercing depth of the lancet, at least in a practically usable piercing depth range settable using the control unit, is not delimited by a mechanical piercing depth stop.

The lancet device according to these teachings comprises a system in which the energy required for executing a piercing movement is already stored in mechanical form, for example, in a drive spring comprised by the drive, the drive spring being able to be retained in a tensioned state by the magnetic retention force, and being controlled and modulated by an electromagnetic actuator, which requires significantly less power. The lancet drive thus preferably comprises an electromagnetic actuator acting on the movement of the lancet (or the lancet guide which holds the lancet), which is actuable by the control unit to regulate the piercing depth in such a way that the lancet piercing movement is modulated by an adjustable thrust and/or adjustable braking.

Starting from a spring-mass system having high mechanical quality factor, i.e., low internal damping, one embodiment of a lancet device according to these teachings may be constructed as follows and/or take the following ideas into consideration.

The drive plunger for a lancet, preferably a magazined lancet, i.e., a lancet stored and provided in a magazine, is relatively high in mass. It hangs in a spring configuration, which allows it to oscillate freely from a retracted position into an extended position. The forwardmost position corresponds to the maximal exit distance of the lancet. The spring constant of the spring configuration is dimensioned in such a way that the plunger has a velocity of approximately 2 m/s at the beginning of the exit of the lancet if the plunger (or lancet guide) is let go from the rearmost, tensioned position.

Furthermore, the drive plunger contains a permanent magnet mounted fixed on or in the plunger. An electromagnet having an iron core is located adjoining the retracted position of the plunger. The magnet in or on the plunger and the iron core are dimensioned in such a way that the plunger is retained in the retracted position against the spring force of the spring configuration when the plunger magnet comes into contact with the iron core. As long as the plunger magnet has a small distance of less than 2 mm, for example, preferably less than 1.0 mm to 0.5 mm to the iron core, however, the attraction force between iron core and plunger magnet is insufficient to retain the lancet plunger or even to draw it backward to the iron core.

A further coil, which detects the movement status of the plunger, may be located along a part of the oscillation path of the plunger magnet, preferably along the entire oscillation path of the plunger magnet. The function of this further coil may also be assumed if necessary by the electromagnet and/or its coil, so that this additional coil need not be present.

After the assembly of the device or possibly after a strong impact on the device, the plunger is located freely hanging in the spring configuration, i.e., it does not press against the iron core of the electromagnet. To tension the system, the plunger having the electromagnet is set into oscillation until the plunger magnet reaches the iron core. The plunger having the plunger magnet is preferably "built up" in resonance by a corresponding powering of the electromagnet. However, the iron core does not have to be reversed in polarity in resonance with the plunger magnet. Powering and turning off in the correct cycle to generate an acceleration force in the direction toward the iron core is sufficient and simplifies the associated electrical circuit.

When the magnet is placed on the core, a voltage peak is induced in the winding, which is used as a signal to turn off the oscillation excitation. The piercing system is now charged with the required energy, and the spring is tensioned and ready for triggering a piercing procedure.

For triggering, the electromagnet is activated using a current pulse in such a way that the iron core is polarized opposite to the permanent magnet, so that the retention force no longer manages against the spring tension and the plunger detaches from the iron core. The spring-mass system then swings through forward, causes the lancet to penetrate a sterile protector that may be provided, and pierces the needle tip of the lancet into the skin. Energy is thus lost from the oscillating system. The system is therefore preferably to be dimensioned in such a way, for example, in regard to the moved masses and the spring tension force, that this energy loss occurring during a piercing procedure, which is also subject to variations because of a varying toughness of the sterile protection, a differing piercing resistance of the skin, or an irregular sharpness of the needle tip, only makes up a small percentage of the total energy in the system as much as possible. For this purpose, it is advantageous if the plunger has a high mass. The exit distance is thus only corrupted or altered very little because of the cited influencing parameters. However, this also means simultaneously that the kinetic energy of the triggered plunger is nearly sufficient so that the plunger magnet reaches the iron core again during the retraction movement.

In order that the plunger magnet also reliably reaches the iron core again, some energy is advantageously supplied to the oscillating system. For this purpose, the electromagnet or possibly an additional detector coil detects the retraction velocity of the plunger and a regulating processor powers the electromagnet at the end of the backswing, e.g., in the last half of the backswing, at least (or precisely) enough that the plunger magnet is securely placed on the iron core, but without noticeable residual velocity and thus without noticeable noise generation, and is again retained thereby.

The exit distance of the lancet when performing a piercing movement may either be set mechanically, e.g., by an adjustable skin contact, in relation to which the lancet exits, or by controlling the powering of the electromagnet upon triggering the piercing, i.e., selectively varying the magnetic force. For example, the electromagnet may be switched very rapidly to repel the permanent magnet, and the spring-mass system then swings loose unobstructed and reaches the full exit distance. Alternatively, the electromagnet may be brought only slowly to the required triggering field strength, so that the plunger magnet is still braked by a residue of the iron attraction on the starting path of its route after the separation from the iron core, for example, on the first 2 mm. The spring-mass system thus loses energy and does not oscillate through to the full exit distance. This may be supported by the shaping of the pole surface of the iron core, so that the permanent magnet is already subject to noticeable attraction upon approach to a few millimeters distance, although this attraction is not sufficient to completely manage against the drive spring.

Alternatively, the spring-mass system may be designed in such a way that only the smallest settable exit distance is reached in free oscillation. The strength of the repulsion by the electromagnet may then give the lancet plunger the additional swing required for the desired exit distance. If this course is selected, the pole surface of the iron core may be a simple planar surface.

In both embodiments, the exit distance is determined by modulation of the triggering by the electrical tensioning drive, i.e., by a control unit. The actual drive and/or main drive of the piercing is performed by the spring force of the spring configuration, the piercing movement being modulated by the control unit.

In a further embodiment, a second electromagnet or a permanent magnet may additionally be situated in the area of the forward dead center position of the piercing movement of the plunger magnet, by which the return of the plunger after reaching the reversal point is braked more or less strongly or may be accelerated in the direction of the return movement. This additional electromagnet or permanent magnet approximately corresponds in its function to a stop, known from the prior art, which delimits the piercing movement, but dampens and/or accelerates the movement of the plunger without noises or a mechanical stop. Special movement curves may thus also be implemented.

However, in this embodiment, the final position of the plunger after the piercing procedure is possibly not the iron core of the rear electromagnet, but rather the free middle position of the spring-mass system. This position is then, of course, to be situated sufficiently far in front of the beginning of the exit of the lancet out of the device so that the lancet does not project out of the device. In addition, in this case the spring-mass system must be built up back into the starting position before using the device, from which a higher energy consumption results and, in addition, the additional braking electromagnet must apply nearly the entire energy of the piercing drive to stop it.

Using a device according to these teachings, a lancet is displaceable along a piercing path to generate a piercing wound in a skin surface to obtain body fluid for diagnostic purposes. The device comprises a lancet drive having drive mechanism for generating a drive force for a piercing movement of the lancet along the piercing path in the direction toward the skin surface. The lancet drive may comprise a magnet, by which a magnetic retention force oriented opposite to the drive force may be generated, and the lancet drive may also comprise a trigger or trigger mechanism, by which the retention force may be reduced enough that the lancet is accelerated in the direction toward the skin surface under the effect of the drive force generated by the drive mechanism.

A drive spring may be used as the drive mechanism, which may be held in a tensioned state by the magnetic retention force. In a lancet device according to an exemplary embodiment, the lancet may be retracted into its starting position via the magnetic retention force after penetration into the skin surface. The retention force may be generated using an electromagnet, for example, or originate from a permanent magnet. If a permanent magnet is used, it is advantageous if the trigger mechanism comprise a coil, by which a magnetic field may be generated, which at least partially, preferably completely compensates for the retention force of the permanent magnet. In the embodiments shown in FIGS. 1-5, a coil is used to form a trigger 5. Through suitable dimensioning of the permanent magnet and the coil, the retention force generated by the magnet may be sufficiently great to cause renewed tensioning of the drive spring after completed piercing.

Furthermore, a coil may be used as the drive mechanism for a lancet device according to the present invention, to generate the drive force magnetically. The coil may also be used as the triggering mechanism, which overcompensates for the magnetic retention force. The magnetic retention force is preferably generated by a permanent magnet, to which a further permanent magnet is assigned as the second part of the drive mechanism as a drive magnet having reversed polarization, so that the magnetic fields of the permanent magnets are destructively superimposed. In this way, the drive force generated by the drive magnet is compensated for by the permanent magnet generating the retention force, so that no resulting drive force and therefore also no lancet movement results without coil current. If a current flows through the drive coil, the magnetic field of the drive magnet is superimposed constructively on the magnetic field of the coil, so that a resulting drive force to accelerate a lancet arises.

Even if the two permanent magnets compensate for one another exactly, a greater drive force may surprisingly be generated by the use of a drive coil in combination with oppositely polarized permanent magnets than using a drive coil alone. By superimposing the coil field with the fields of the oppositely polarized permanent magnets, an increased magnetic field strength results locally in a first area and a locally reduced field strength results in a second area. The locally increased magnetic field strength may be used for the purpose of magnetizing a drive element, such as a soft-magnetic coil core. The force exerted by the magnetic field on the drive element is greater overall because of the locally increased field strength than if a coil is used without permanent magnets.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIG. 1 is a side sectional view of a first exemplary embodiment of a lancet device according to the present invention with relaxed drive spring;

FIG. 2 is a side sectional view of the exemplary embodiment shown in FIG. 1 with a tensioned drive spring;

FIG. 3 is a side sectional view of the exemplary embodiment shown in FIG. 1 with a lancet shown piercing into a body part;

FIG. 4 is a graph illustrating the voltage curve in the coil of the exemplary embodiment shown in FIG. 1; and FIG. 5 is a side sectional view of a second exemplary embodiment of a lancet device according to the present invention with relaxed drive spring.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The lancet devices 1 illustrated in FIGS. 1 through 3 and in FIG. 5 may be integrated in a handheld analysis device, for example, which has a measuring apparatus for assaying body fluid, which is obtained from a generated piercing wound. The lancet devices may also be installed in a separate device such as a puncture aid.

The central component of the lancet device 1 shown in FIGS. 1 through 3 is a lancet drive 2, which comprises a pushrod 3, which may also be referred to as a lancet guide, which is configured to hold a lancet 10 by means of lancet holder 8. A drive mechanism is provided in the form of a drive spring 4 or a pair of springs for forward and return stroke, a coil 5 having an iron yoke 6, and a permanent magnet 7 situated axially in the coil 5. The pushrod 3 is preferably made of a magnetically neutral material, more preferably, from an electrically nonconductive material, and particularly preferably, from plastic, to avoid eddy current losses during the movement in the magnetic field. Pushrod 3 carries this permanent magnet 7 and/or plunger magnet 7. Pushrod 3 also comprises a lancet holder 8 having a replaceable lancet 10 and is accelerated along a piercing path predefined by the guide 11 to generate a piercing wound using the drive spring 4, which is implemented as a coiled spring. In alternative embodiments, the pushrod 3 may carry an armature plate made of an iron or another ferromagnetic material, by which a magnetic circuit is closed in the tensioned position shown in FIG. 2 by the iron yoke 6 and possibly a pole shoe enclosing the coil 6. If the armature plate is implemented as a permanent magnet (plunger magnet 7), it may not only be attracted by the iron yoke 6, but rather also repelled and additionally accelerated by a magnetic field generated by the coil 5.

The lancet 10 is removably fastened on the lancet holder 8 on the pushrod 3. The permanent magnet 7 is permanently attached thereto. In general, the lancet drive 2 may comprise an armature plate 7 which is situated on a pushrod 3 carrying the lancet 10 and is formed from iron, another ferromagnetic material, or as a permanent magnet. In the illustrated embodiments, permanent magnets are used to form the armature plate 7. Corresponding to the magnet 7 (coaxially around the guide 11 here), an iron yoke 6 and the coil 5 are mounted fixed on the frame. The pushrod 3 is equipped with a spring 4 or a pair of springs for forward and return strokes, whose fixed end is fastened to the frame 12. The skin contact 13 is also situated on the frame 12. The coil 5 is used as a retention coil of the retention mechanism and has a coil core 6 which is magnetizable or implemented as a permanent magnet. The pushrod 3 projects into the coil core formed by the iron yoke 6, which forms a guide 11 for the pushrod 3.

In addition to the drive spring 4, the lancet drive 2 may also comprise a restoring spring (not shown) for generating a retraction movement of the lancet 10. The drive spring 4 is tensioned again by the retraction movement. Drive spring 4 and the optional restoring spring may each be implemented as coiled springs which enclose the pushrod 3. The drive spring 4 and possibly the restoring spring are each supported at one end on a support section of the pushrod 3, which is implemented as a thickened part 15 in the exemplary embodiment shown, and at the particular other end on the frame. The drive spring 4 and the restoring spring may be situated in such a way that relaxation of the drive spring 4 causes tensioning of the restoring spring and relaxation of the restoring spring causes tensioning of the drive spring 4. The term "tensioning" is to be understood in this context to mean that energy is stored in the particular effective spring. This may be caused, for example, by compression in a compression spring and by stretching in an expansion spring or by bending in a leaf spring.

In other embodiments, the drive mechanism may also comprise a drive coil having a coil core, which is magnetizable or implemented as a permanent magnet, in addition to or instead of the drive spring 4. For example, in FIG. 1, the coil 5 having the iron yoke 6 may also assume or contribute to the function of the drive mechanism. Furthermore, the drive coil and the retention coil may be the same coil.

In FIG. 1, the lancet device is shown with relaxed drive spring 4. To tension the lancet device 1, the spring-mass system made of plunger 3 and spring 4 is built up by fed-back alternating powering of the coil 5 until the plunger magnet 7 comes into contact with the iron core 6 (FIG. 2). In this state, the coil 5 may remain unpowered, the plunger magnet 7 is retained fixed against the tensioned spring 4 on the iron yoke 6.

The pushrod 3 is shown in its position with tensioned drive spring 4 in FIG. 2. The drive spring 4 is a coiled spring which acts on a pushrod 3 carrying the lancet 10. The pushrod 3 and/or the drive spring 4 is retained in this position by the magnetic retention force of the iron yoke 6 integrated in the coil core of the coil 5 or a permanent magnet. The coil core is situated fixed in place in relation to the coil 5. The lancet device 1, by which the lancet 10 is displaceable along a piercing path to generate a piercing wound in a skin surface, in particular to obtain body fluid for diagnostic purposes, thus comprises a lancet drive 2, which has a drive mechanism for generating a drive force for a piercing movement of the lancet along the piercing path in the direction toward the skin surface, a retention mechanism for generating a magnetic retention force for retaining the lancet 10 in a tensioned position, and a triggering mechanism, by which the retention force is reducible enough that the lancet is accelerated in the direction toward the skin surface under the effect of the drive force generated by the drive mechanism, and has a control unit 18 for regulating the piercing depth of the lancet 10, by which the reduction of the retention force is controllable in such a way that the desired piercing depth of the lancet 10 results as a function of the control unit 18 during the triggered piercing movement.

The coil 5 is used as the triggering mechanism for triggering a piercing movement. A magnetic field is generated by causing an electric current to flow through the coil 5, which compensates for the retention force of the plunger magnet 7, so that the drive spring 4 relaxes and the pushrod 3 having the lancet 10 is accelerated in the direction toward the skin surface under the effect of the drive force generated by the drive spring 4.

The piercing procedure is illustrated in FIG. 3. For the piercing, the coil 5 is impinged by a current pulse, so that the retention force of the permanent magnet 7 on the iron yoke 6 is overcome. The piercing depth into the skin 14 may be controlled by a control unit via the strength and duration of this pulse. If necessary, the velocity of the retraction may also be slowed, in that a countercurrent is applied at a given time. The controller does not require a path sensor or any position detection for this purpose, but rather only information about the velocity in the movement direction, which may be acquired via the mutual induction in the coil 5, for example.

It is possible to tension the spring and vary the piercing depth by regulated "powering." The triggering may be used for the purpose of modulating the piercing distance (e.g., by an electromagnetic thrust for greater exit distances and/or a braking for lower exit distances). The coil 5 is thus used as a type of electromagnetic actuator of the lancet drive 2 acting on the movement of the lancet 10, the actuator being able to be driven by the control unit to regulate the piercing depth in such a way that the lancet piercing movement is modulated by an adjustable thrust and/or adjustable braking.

Even in a malfunction, the possibility exists of moving the pushrod 3 from an intermediate position shown in FIG. 1 back into the tensioned initial position shown in FIG. 2 in that a mechanical oscillation of the mechanical system formed by the drive spring 4, the pushrod 3, and possibly a restoring spring is excited using the coil 5 by periodic current surges. Upon continued excitation at the resonance frequency of this system, the amplitudes of this oscillation increase until the pushrod 3 returns into the starting or initial position shown in FIG. 2 and may be held there by the magnetic retention force in the tensioned position, namely by the retention force of the plunger magnet 7 on the iron yoke 6.

It may be established by a measurement of the inductivity of the coil 5 whether the plunger magnet 7 presses against the iron yoke. In this way, it may thus be ascertained whether or not the pushrod 3 is located in the tensioned position shown in FIG. 2. The inductivity of the coil 5 is preferably measured shortly after a piercing, for example, 1 to 2 seconds after a piercing. If it is established that the pushrod 3 is not located in the tensioned position, a mechanical oscillation of the mechanical system formed by the drive spring 4 and the pushrod 3 is excited by periodic current surges, so that the pushrod 3 returns into its tensioned position.

In this way, the coil 5 is used as a position sensor for the position of the pushrod 3. The illustrated lancet device 1 may alternatively or additionally also be equipped with other position sensors, so that the optimal instant for turning off or reversing the polarity of the current through the coil 5 may be ascertained as a function of the instantaneous position of the pushrod 3. The use of sensors therefore allows, instead of simple control of the coil current, in which a predefined profile is predefined for a current pulse, regulation of the coil current as a function of the position of the pushrod 3.

In general, it may be advantageous if a magnetic field may be generated by the electromagnetic actuator, which partially compensates, completely compensates, or overcompensates for the retention force to control the piercing depth of the lancet 10. In exemplary embodiments, the electromagnetic actuator comprises an actuator coil, possibly having a coil core which is magnetizable or implemented as a permanent magnet. At least two coils of the drive coil, the retention coil, and the actuator coil may be the same coil to save components.

Furthermore, a mechanical stop is not provided to delimit the exit distance of the lancet 10, as has been known up to this point from ballistic piercing aids. Instead, the resonant system made of pushrod 3 and lancet 10 is designed in such a way that the lancet 10 swings through up to its oscillation reversal point. The pushrod 3 having the lancet 10 is implemented to oscillate freely in the piercing direction up to an oscillation reversal point, so that the piercing depth of the lancet 10 is not delimited by a mechanical piercing depth stop, at least in a practically usable piercing depth range settable using the control unit. The lancet device 1 with the pushrod 3 in the piercing position is shown in FIG. 3. In the piercing position, there is no stop, for example, formed by the plunger magnet 7, that presses against a delimitation element of the guide 11, so that the piercing path is not thus delimited. Of course, the illustrated system made of pushrod 3 and plunger magnet 7 reaches a mechanical stop point, which delimits further movement, in the event of further movement in the piercing direction exceeding normal operation. Thus, for example, the pushrod 3 may have a thickened part 15, which hits the iron yoke 6, to prevent a user from pulling out the pushrod 3. However, the oscillation is not delimited by this stop during proper use of the lancet device 1.

Furthermore, the energy in the system obtained once by build up oscillation may be retained. Once caused to move, the plunger 3 oscillates back and forth. On the return path, only little energy is required to capture it again. This means that the excess energy is not dissipated as typical up to this point (e.g., converted into heat using dampers), but is instead stored as spring tension until the next piercing. It only has to be built up back into the system in case of failure of the retention magnet, wherein a mechanical oscillation of the lancet 10 is excited after a completed piercing by periodic current surges using the control unit, by which a pushrod 3 carrying the lancet 10 returns back into its initial position, in which it is retained by the magnetic retention force in the tensioned position. The lancet drive 2 thus advantageously comprises an actuator, which is controllable using the control unit in such a way that the lancet 10 may be accelerated in a retraction movement opposite to the piercing movement after performing a piercing in such a way that the lancet 10 returns into the initial position, in which it is held in the tensioned position by the magnetic retention force.

Of course, friction forces arise in the illustrated lancet device 1, so that the energy stored in the piercing position shown in FIG. 3, and possibly also in an additional restoring spring, is not entirely sufficient for renewed tensioning of the drive spring 4. In the illustrated device, the retraction movement of the pushrod 3 is therefore supported by the control unit. The acceleration exerted by the coil 5 on the plunger magnet 7 in the retraction movement suffices to bring the pushrod 3 back into the tensioned position illustrated in FIG. 2 and to tension the drive spring 4 at the same time.

To support the retraction movement, the direction of the current flowing through the coil 5 to trigger a piercing may be reversed in polarity, so that the magnetic field generated by the coil 5 is added to the retention force of the plunger magnet 7. To reverse the polarity of the current, for example, a control unit having an H bridge may be used. For example, the reversal of polarity occurs in the moment at which the lancet 10 has reached the outermost point of the piercing path.

The lancet device 1 according to the present invention is thus implemented according to an advantageous additional feature in such a way that the lancet drive 2 and the lancet 10, in particular a pushrod 3 carrying the lancet 10, the lancet 10, and the drive mechanism, which includes the drive spring 4 in the exemplary embodiment illustrated, form an oscillating system which may oscillate along the piercing path. It is advantageously provided that the oscillation energy contained in the oscillation system when performing a piercing using the lancet 10 is recuperated to a great extent and is stored as potential energy by renewed tensioning, occurring following the piercing, of the drive means in an initial position of the drive means, so that the reclaimed kinetic energy is available to perform a following piercing and does not have to be applied again. The energy required to perform a piercing is approximately 1.0 mJ to 5.0 mJ, typically 2.5 mJ. The oscillation energy of the oscillating system is advantageously at least 10×, preferably at least 50×, and especially preferably at least 100× as large as the required piercing energy. The typical oscillation energy is thus between 25 mJ and 250 mJ.

A piercing and retraction movement of the lancet 10 typically lasts a total of 4 ms to 6 ms. For the most rapid possible piercing movement, a correspondingly strong drive spring 4 and a correspondingly strong plunger magnet 7, such as a rare earth magnet, may be utilized. To compensate for the magnetic retention force, voltages and/or current strengths which greatly exceed the performance capability of commercially available batteries are therefore preferably used. The coil 5 is therefore connected via current buffers and/or voltage converters to an internal current source of the lancet device 1, such as a battery, so that a current pulse capable of compensating for the magnetic retention force may be generated through the coil 5 by the control unit using commercially available batteries. For example, capacitors or accumulators, in particular lithium-polymer accumulators, are suitable as current buffers. Suitable voltage converters are available as DC/DC converters. The corresponding technology for generating intensive current pulses is typical in cameras for generating light flashes, for example, and may be used for the described lancet device 1.

FIG. 4 shows the voltage curve in the coil 5 of the exemplary embodiment shown in FIG. 1.

An alternate exemplary embodiment of the lancet device 1 is illustrated in FIG. 5. It has a "relay-type" lancet drive 2, in which the coil 5 is situated on a U-shaped iron yoke 6. The guide 11 of the plunger 3 is displaceable and/or oscillates back and forth. It is not formed by the iron yoke 6, but rather is situated separately therefrom. The drive spring 4, which acts on the pushrod 3 carrying the lancet 10, is not a coiled spring in this case, but rather a leaf spring. It is clamped fixed at one end on the frame 12 and connected at the other end to a dog 16, which engages in a receptacle 17 of the plunger 3. Of course, in addition to the leaf spring, coiled springs which engage on the dog 16, the receptacle 17, or the plunger 3, may also be provided.

The dog 16 carries a permanent magnet 7 which may be attracted or held by the iron yoke 6, as a function of the activation of the coil 5 by the voltage U, which is varied as a function of the time t.

The further design of the second exemplary embodiment shown in FIG. 5 may be made in accordance with the first embodiment illustrated in FIGS. 1 through 3. The lancet device with relaxed drive spring 4 is illustrated in FIG. 5. To tension the lancet device 1, a magnetic field is generated using the coil 5 and the iron yoke 6, by which the permanent magnet 7 is attracted until it comes into contact with the iron yoke 6. In this state, the coil 5 may remain unpowered, the permanent magnet 7 is retained fixed against the tension spring 4 on the iron yoke 6.

The coil 5 is also used as the triggering means for triggering a piercing movement. A magnetic field is generated by causing an electric current to flow through the coil 5, which compensates for the retention force of the permanent magnet 7, so that the drive spring 4 relaxes and the pushrod 3 having the lancet 10 is accelerated under the effect of the drive force generated by the drive spring 4 via the dog 6 and the receptacle 17 on the pushrod 3 in the direction toward the skin surface. The piercing depth into the skin may also be controlled here by a control unit via the strength and duration of the pulse applied to the coil 5. It is also possible, if necessary, to build up the resonant system into tension by suitable powering, such as was described above with reference to FIGS. 1 through 3.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

1 lancet device
2 lancet drive
3 pushrod
4 drive spring
5 coil
6 iron yoke
7 permanent magnet
8 lancet holder
10 lancet
11 guide
12 frame
13 skin contact
14 skin
15 thickened part
16 dog
17 receptacle
U voltage
t time

What is claimed is:

1. A lancet device for generating a piercing wound in a skin surface to obtain a body fluid, comprising:
   a lancet guide configured to hold a lancet;
   a lancet drive for generating a drive force to move the lancet guide along a piercing path in a piercing direction;
   a retention mechanism for generating a magnetic retention force for retaining the lancet guide in a tensioned position;
   a trigger, actuation of which reduces the retention force and thereby allows the drive force to accelerate the lancet guide in the piercing direction;
   a control unit which controls the reduction in retention force and thereby regulates piercing depth wherein the piercing depth is not affected by a mechanical piercing depth stop; and
   wherein the lancet drive stores mechanical energy for moving the lancet guide along the piercing path when the lancet drive is placed in the tensioned position.

2. The lancet device of claim 1, wherein the lancet guide advances freely in the piercing direction up to an oscillation reversal point.

3. The lancet device of claim 1, wherein the lancet drive comprises a drive spring.

4. The lancet device of claim 1, wherein the lancet drive comprises an armature plate positioned on the lancet guide, the armature plate being formed from magnetic material.

5. The lancet device of claim 1, wherein the trigger comprises an electromagnetic actuator driven by the control unit, the electromagnetic actuator regulating the piercing depth by adjustable thrust, adjustable braking, or combinations thereof.

6. The lancet device of claim 5, wherein the electromagnetic actuator generates a magnetic field which counters the retention force.

7. The lancet device of claim 5, wherein the control unit is configured to drive the actuator to accelerate the lancet guide in a retraction movement opposite the piercing movement after performing a piercing such that the lancet guide returns to the tensioned position in which it is retained by the magnetic retention force.

8. The lancet device of claim 1, wherein the lancet guide oscillates along the piercing path during use.

9. The lancet device of claim 8, wherein the lancet guide returns to the tensioned position with the aid of oscillation energy from the lancet guide and lancet drive, whereby energy used for the piercing movement is at least partially recaptured and stored as potential energy for use with subsequent piercing movements.

10. The lancet device of claim 9, wherein energy stored in the lancet guide and lancet drive in the tensioned position is significantly greater than an amount of energy required to perform a piercing operation.

11. A method for operating a lancet device having a lancet guide that holds a lancet and a lancet drive for generating a drive force to move the lancet guide along a piercing path in a piercing direction, the method comprising:
   positioning the lancet drive in a tensioned position;
   retaining the lancet drive in the tensioned position with a magnetic force;
   selecting a desired piercing depth;
   selectively varying the magnetic force to release the lancet drive from the tensioned position and to cause the lancet to advance to and reverse direction at the desired piercing depth wherein the desired piercing depth is selectively variable by the selective variation of the magnetic force; and
   wherein the lancet drive stores mechanical energy for moving the lancet guide along the piercing path when the lancet drive is placed in the tensioned position.

12. The method of claim 11, wherein the step of selectively varying the magnetic force comprises reducing the magnetic force, wherein a force acting on the lancet by the lancet drive overcomes the magnetic force, the force acting on the lancet advancing the lancet in the piercing direction.

13. The method of claim 12, wherein the lancet oscillates freely in the piercing direction up to the desired piercing depth.

14. The method of claim 12, wherein the step of selectively varying the magnetic force comprises repelling the lancet in the piercing direction.

15. The method of claim 11, wherein the step of selectively varying the magnetic force comprises selecting a speed at which to reduce the magnetic force.

16. The method of claim 11, wherein the step of selectively varying the magnetic force comprises thrusting the lancet in the piercing direction.

17. The method of claim 11, wherein the step of selectively varying the magnetic force comprises providing a braking force for the lancet.

18. The method of claim 11, wherein the step of selectively varying the magnetic force further comprises accelerating the lancet in a retraction movement opposite the piercing movement to return the lancet drive to the tensioned position.

19. A lancet device for generating a piercing wound in a skin surface, comprising:
   a lancet guide configured to hold a lancet;
   a lancet drive for generating a drive force to move the lancet guide along a piercing path in a piercing direction, the lancet drive comprising a drive spring;
   a magnet associated with the lancet drive;
   an electromagnet releasably coupled to the magnet when the lancet drive is in a tensioned position;
   a control unit operably connected to the electromagnet, the control unit selectively varying a magnetic force between the electromagnet and the magnet as a function of desired piercing depth, wherein the lancet guide advances freely in the piercing direction up to an oscillation reversal point; and
   wherein the lancet drive together with the lancet guide and lancet form an oscillatory spring-mass system.

20. The lancet device of claim 19, wherein the magnet is attached to the lancet guide.

21. The lancet device of claim 20, wherein the magnet comprises an armature plate formed from magnetic material.

22. The lancet device of claim 19, wherein, after a piercing movement of the lancet guide, the control unit varies the magnetic force to accelerate the lancet guide in a retraction movement opposite the piercing movement to return the lancet drive to the tensioned position.

23. The lancet device of claim 19, wherein the control unit reduces the magnetic force, which causes a force provided by the drive unit to overcome the magnetic force, wherein the lancet drive accelerates the lancet guide in the puncturing direction.

24. The drive spring of claim 19, wherein the lancet drive comprises a leaf spring.

25. The lancet device of claim 24, wherein the magnet is attached to the leaf spring.

* * * * *